United States Patent
Akahoshi

(10) Patent No.: US 9,132,033 B2
(45) Date of Patent: *Sep. 15, 2015

(54) PHACOEMULSIFICATION NEEDLE

(75) Inventor: Takayuki Akahoshi, Tokyo (JP)

(73) Assignee: ART, LIMITED, Grand Cayman (KY)

( * ) Notice: Subject to any disclaimer, the term of this patent is extended or adjusted under 35 U.S.C. 154(b) by 581 days.

This patent is subject to a terminal disclaimer.

(21) Appl. No.: 12/263,315

(22) Filed: Oct. 31, 2008

(65) Prior Publication Data

US 2011/0172588 A1  Jul. 14, 2011

Related U.S. Application Data

(60) Provisional application No. 60/984,375, filed on Nov. 1, 2007.

(51) Int. Cl.
  *A61F 9/007*  (2006.01)
  *A61M 1/00*  (2006.01)
  *A61B 17/32*  (2006.01)

(52) U.S. Cl.
  CPC .......... *A61F 9/00745* (2013.01); *A61F 9/00763* (2013.01); *A61M 1/0039* (2013.01); *A61B 2017/320072* (2013.01); *A61B 2017/320096* (2013.01)

(58) Field of Classification Search
  CPC ....... A61B 2017/320072; A61B 2017/320096; A61B 2017/320088; A61B 2017/320076
  USPC ...................... 604/22, 118, 119, 542, 35, 264; 606/107, 169
  See application file for complete search history.

(56) References Cited

U.S. PATENT DOCUMENTS

| | | | | |
|---|---|---|---|---|
| 4,961,424 A * | 10/1990 | Kubota et al. | ...................... | 601/2 |
| 5,478,328 A * | 12/1995 | Silverman et al. | ............ | 604/272 |
| 5,676,649 A * | 10/1997 | Boukhny et al. | ................ | 604/22 |
| 5,725,495 A * | 3/1998 | Strukel et al. | .................... | 604/44 |
| 5,741,226 A * | 4/1998 | Strukel et al. | .................... | 604/35 |
| 5,743,871 A * | 4/1998 | Strukel et al. | .................... | 604/35 |
| 5,993,408 A * | 11/1999 | Zaleski | ............................ | 604/22 |
| 6,007,513 A * | 12/1999 | Anis et al. | ........................ | 604/22 |
| 6,007,555 A * | 12/1999 | Devine | ............................ | 606/169 |
| 6,165,150 A * | 12/2000 | Banko | .............................. | 604/22 |
| 6,402,769 B1 * | 6/2002 | Boukhny | ........................ | 606/169 |
| 6,533,750 B2 * | 3/2003 | Sutton et al. | ..................... | 604/22 |
| 8,764,782 B2 * | 7/2014 | Akahoshi | ........................ | 606/169 |
| 2002/0099325 A1 * | 7/2002 | Sutton et al. | ..................... | 604/22 |
| 2006/0052758 A1 * | 3/2006 | Dewey | ............................ | 604/272 |
| 2007/0249942 A1 * | 10/2007 | Salehi et al. | .................. | 600/471 |
| 2008/0058708 A1 * | 3/2008 | Akahoshi | .......................... | 604/22 |
| 2008/0294087 A1 * | 11/2008 | Steen et al. | ...................... | 604/22 |
| 2009/0143795 A1 * | 6/2009 | Robertson | ...................... | 606/169 |
| 2010/0010419 A1 * | 1/2010 | Akahoshi | .......................... | 604/22 |
| 2011/0015561 A1 * | 1/2011 | Akahoshi | .......................... | 604/22 |
| 2011/0166502 A1 * | 7/2011 | Nallakrishnan | ................. | 604/22 |

* cited by examiner

Primary Examiner — Bhisma Mehta
Assistant Examiner — Jenna Zhang
(74) Attorney, Agent, or Firm — Wood, Phillips, Katz, Clark & Mortimer

(57) ABSTRACT

A phacoemulsification needle having a central, hollow passageway terminates in a straight, enlarged needle tip formed off-axis from the passageway, allowing the needle tip to move eccentrically when the needle is subjected to torsional vibratory motion.

13 Claims, 4 Drawing Sheets

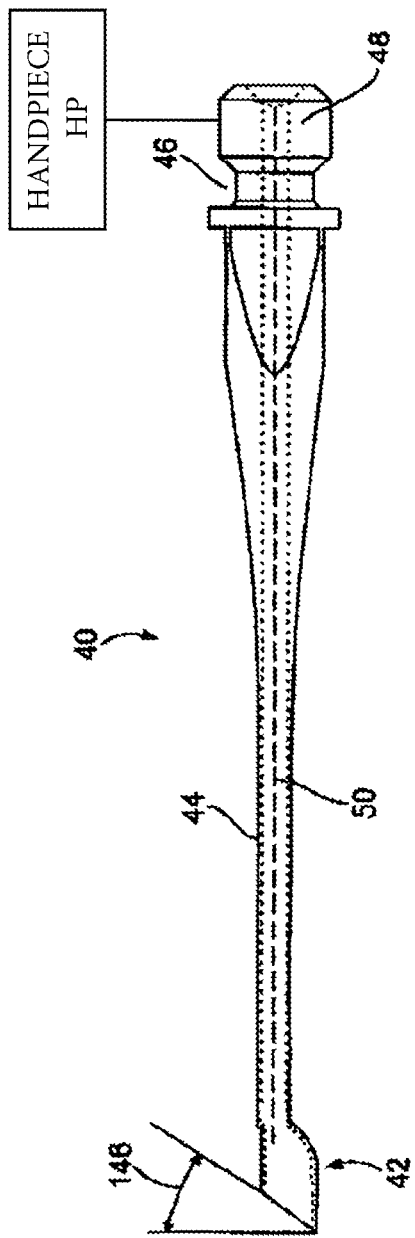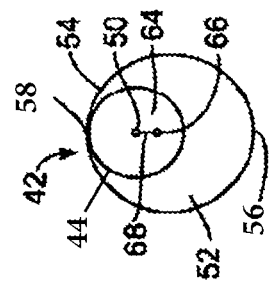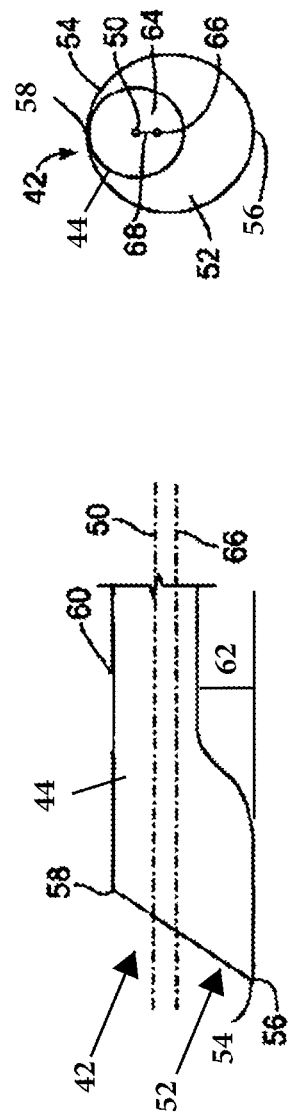
FIG. 3
FIG. 5
FIG. 4

PHACOEMULSIFICATION NEEDLE

This application claims priority from U.S. Provisional Patent Application Ser. No. 60/984,375, filed Nov. 1, 2007, which is incorporated herein in its entirety by reference.

FIELD OF THE INVENTION

This disclosure relates to surgical instruments and surgical techniques used in eye surgery and more particularly, to phacoemulsification apparatus and methods for their use.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece to which is attached a hollow needle. Electrical energy is applied to vibrate the needle at ultrasonic frequencies in order to fragment the diseased lens into small enough particles to be aspirated from the eye through the hollow needle. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse.

Phacoemulsification needles and tips are well represented in the prior art. Needles and tips of varying configurations are well known. A particular shape for a tip or needle is often dictated by the type of handpiece with which the needle is to be used.

U.S. Pat. No. 5,725,495 (Strukel et al) teaches and describes a phacoemulsification handpiece, sleeve and tip illustrating a wide variety of tip configurations and needle cross-sectional configurations.

U.S. Pat. No. 6,007,555 (Devine) teaches and describes an ultrasonic needle for surgical emulsification. The needle and its tip are shown in both circular and oval configurations.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

U.S. Pat. No. 5,645,530 (Boukhny) teaches and describes a phacoemulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

Published U.S. Patent Application No. 2003/0004455 (Kadziauskas) teaches and describes a bi-manual phaco needle using separate emulsification and aspiration needles inserted into the eye simultaneously during surgery.

Published U.S. Patent Application No. 2006/0217672 (Chon) teaches and describes a phacoemulsification tip that is swaged or crimped at its distal end. The tip is intended for use with a handpiece producing torsional motion and the crimping forms cutting edges at the distal end.

Many phacoemulsification needles and tips are designed for use with handpieces that vibrate the needle longitudinally at relatively low frequencies. In addition to longitudinal vibration, the NeoSoniX® handpiece sold by Alcon, Inc. of Ft. Worth, Tex. has a rotational or torsional oscillation vibration frequency of about 100 cycles/second. There are also handpieces that provide torsional oscillation of the phacoemulsification tip at frequencies of about 32,000 cycles/second.

Use of the torsional-type handpiece has called for phaco needle tip designs differing from those used with the longitudinal-type handpiece. For example, needles have been designed with tips that are shaped, swaged and angled to take advantage of the torsional motion created by the handpiece.

Many surgeons favor phacoemulsification needles having the straight tip design most commonly used with longitudinal handpieces but have found that using them with torsional handpieces does not produce good results.

I have found that forming the needle tip in an off-axis position relative to the axis of the needle body causes sufficient eccentric motion, or "wobble" during torsional motion to produce improved phacoemulsification results while retaining the straight-tip configuration.

While the following describes a preferred embodiment or embodiments of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

In accordance with a preferred embodiment of the apparatus a phacoemulsification needle is provided for use with a high-frequency torsional phacoemulsification handpiece with the needle having a straight needle tip with the tip being formed off-axis with respect to the hollow passage formed through the needle.

BRIEF DESCRIPTION OF THE DRAWINGS

Further aspects of the present invention will be best understood by reference to the accompanying drawings in which like numbers are used to identify like parts, and which are presented to illustrate the aspects of the invention although not necessarily to actual scale, wherein:

FIG. 3 is a lateral schematic view of a phacoemulsification needle embodying the present invention;

FIG. 4 is a partial lateral view of the needle tip of FIG. 3;

FIG. 5 is a view taken along 5-5 of FIG. 4;

DETAILED DESCRIPTION OF THE INVENTION

Figure 1:
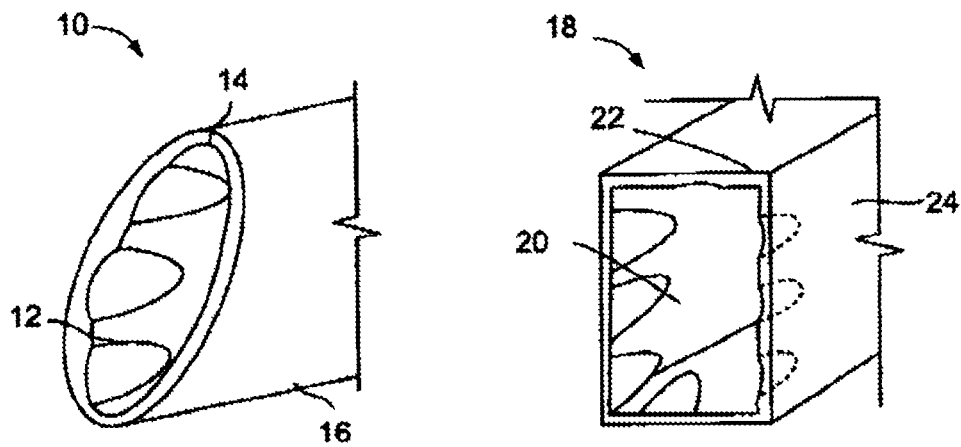
FIG. 1 is a drawing showing prior art straight oval- and square-shaped tips.

Referring now to FIG. 1, the numeral 10 indicates generally a prior art phacoemulsification needle tip as shown in U.S. Pat. No. 6,007,555. Needle 10 terminates in a mouth 12 defined by a lip 14 at the end of needle body 16, with lip 14 and needle body 16 formed as having an oval cross-section configuration.

Referring to FIG. 1, the numeral 18 indicates generally a prior art phacoemulsification needle tip from U.S. Pat. No. 6,007,55, having a mouth 20 defined by a lip 22 at the end of needle 24. The cross-sectional configuration of needle tip 18 and mouth 20 is a rectangle.

Figure 2:
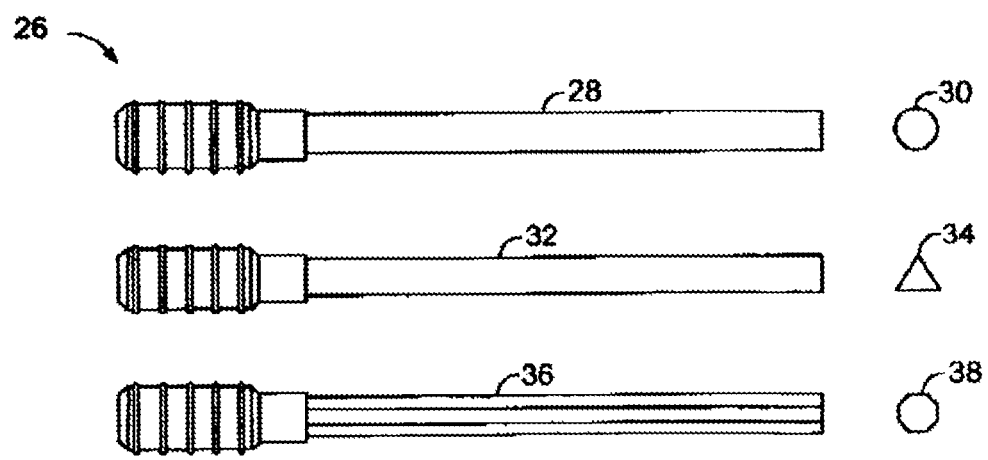
FIG. 2 is a drawing showing several prior art needle cross-sectional configurations.

Referring now to FIG. 2, the numeral 26 identifies several prior art phacoemulsification needles as described in U.S. Pat. No. 5,725,495, with needle 28 having a circular cross-section as shown at 30, needle 32 having a triangular cross-section as shown at 34 and needle 36 having an octagonal cross-section as shown at 38.

Both tips 10 and 18 in FIG. 1 exemplify one form of a "straight" needle tip, that is, a tip that is coaxial with or centered on the hollow aspiration passageway formed through the needle body. Other straight tips are known which have needle tips that are larger in cross-sectional area than the needle's aspiration passageway yet which are centered on the passageway.

Referring now to FIG. 3, the numeral 40 indicates generally a phacoemulsification needle embodying certain aspects of the present invention. Needle 40 has a needle tip 42 formed integrally with a hollow needle body 44 at a distal end thereof. At a proximal end thereof, needle body 44 has a needle end 46 which terminates in a mount 48 which allows needle 40 to be attached to a phacoemulsification handpiece HP configured to impart a torsional ultrasonic vibratory motion to the needle 40.

Referring to FIG. 4, an enlarged detail of tip 42 is shown. As seen in both FIGS. 4 and 5, tip 42 has a mouth 52 defined by a lip 54 which, in the example shown in FIGS. 3 and 4, is formed at a 30° angle 146 to axis 50. The angle shown is one of choice: lip 54 can also be formed perpendicular to axis 50 or any number of other configurations corresponding generally to the configurations of known straight tips presently used with longitudinally-vibrating hand pieces.

As viewed in FIG. 4, tip 52 has a lead portion 56 and a trailing portion 58, with lead portion 56 being that part of lip 54 that extends longitudinally forward past trailing portion 58, while trailing portion 58 is that part of lip 54 that extends the least distance forward. In the example shown in FIG. 4, trailing portion 58 is substantially co-linear with the outer surface 60 of needle body 44, while lead portion 56 is offset by a distance 62 from the outer surface 60 of needle body 44. The effect of forming lip 54 at the angle shown is to place lead portion 56 at the farthest point from needle body axis 50.

Referring now to FIG. 5, the interior 64 of needle body 44 is shown to illustrate the position of axis 50. Tip mouth 52 is shown defined by lip 54 with lead point 56 and trailing point 58. In the example shown, tip 42 has a circular cross-section having its own tip axis 66 extending therethrough. As seen in FIGS. 4 and 5, in this example, axes 50 and 66 do not coincide but are offset by a distance 68. As also seen in FIG. 5, the cross-sectional area of tip 42 is larger than the cross-sectional area of needle body 44 when viewed in a plane perpendicular to axis 50.

In a preferred example needle body 44 is 1.0 mm in exterior diameter with a wall thickness of 0.10 mm, leaving an interior diameter of 0.80 mm. Tip 42 has an exterior diameter of 1.10 mm and a wall thickness of 0.10 mm. The lateral distance from the point at which tip 42 begins to enlarge outward from needle body 44 to lead point 56 is 1.80 mm, while offset distance 62 is 0.30 mm.

Figure 6:
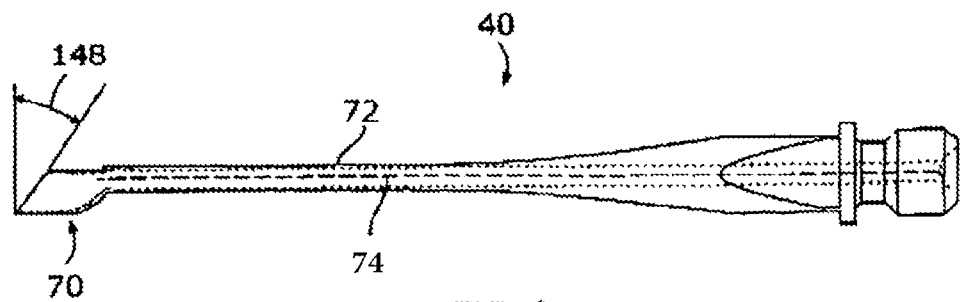
FIG. 6 is a lateral schematic view of a second phacoemulsification needle embodying the present invention.

Referring now to FIG. 6, a second example of a needle tip formed on needle 40 is shown, embodying certain aspects of the present invention. Needle tip 70 is square in cross-sectional shape and is formed integrally with a hollow needle body 72. In the example shown, needle body 72 has a circular cross-section with a longitudinally-extending central axis 74.

Figure 7:
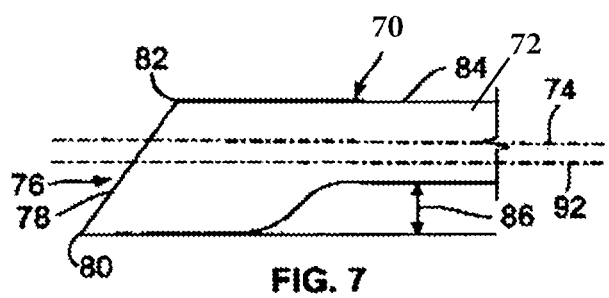
FIG. 7 is a lateral view the needle tip of FIG. 6.

Referring to FIG. 7, an enlarged detail of tip 70 is shown. As seen in both FIGS. 7 and 8, tip 70 has a mouth 76 defined by a lip 78 which, in the example shown in FIGS. 6 and 7, is formed at a 30° angle 148 to axis 74 and has a substantially uniform wall thickness. The angle shown is one of choice: lip 78 can also be formed perpendicular to axis 74 or any number of other configurations corresponding generally to the configurations of known straight tips presently used with longitudinally-vibrating hand pieces.

As viewed in FIG. 7, tip 70 has a lead lip portion 80 and a trailing lip portion 82, with lead portion 80 being that part of lip 78 that extends longitudinally past trailing portion 82, while trailing portion 82 is that part of lip 78 that extends the least distance longitudinally forward. In the example shown in FIG. 7, trailing lip portion 82 is substantially co-linear with the outer surface 84 of needle body 72, while lead lip portion 80 is offset by a distance 86 from the outer surface 84 of needle body 72. The effect of forming lip 78 at angle 148 is to place lead lip portion 80 farthest from needle body axis 94.

The exterior surface of an axially extending length of the tip 70 has a square cross-sectional shape.

Figure 8:
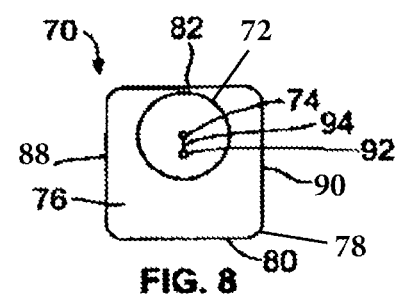
FIG. 8 is a view taken along 8-8 of FIG. 6.

Referring now to FIG. 8, the interior of needle body 72 is shown with axis 74. Mouth 76, defined by lip 68, has a first slanted lip portion 88 extending from lead point 80 to trailing point 82, and a second slanted lip portion 90 disposed opposite lip portion 88 and also extending from lead portion 80 to trailing portion 82. In the example shown, an axial length of tip 70 has a square cross-section having its own central axis 92, which, as seen in FIGS. 7 and 8 is offset from needle body axis 74 by a distance 94. As also seen in FIG. 8, the cross-sectional area of tip 70 is greater than the cross-sectional area of needle body 72 when viewed in a plane perpendicular to axis 74.

Figure 9:
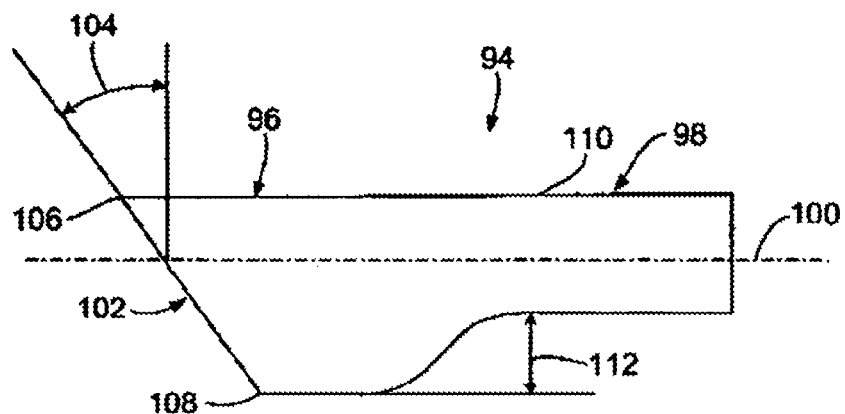
FIG. 9 is a partial lateral view of a variation of the tip shown in FIG. 3.

Referring now to FIG. 9 the numeral 94 identifies a phacoemulsification needle constructed substantially as described with respect to FIGS. 3, 4 and 5. Needle 94 has a tip 96 formed with a circular cross-section and integral with needle body 98. Needle body 98 has a central axis 100.

Tip 96 has a circular mouth 102 which, in this example, is formed at an angle 104 to axis 100. In this example, angle 104 is measured 30° in a direction opposite to that of angle 146 of mouth 52 as shown in FIG. 4. In this configuration, tip 96 has a lead point 106 and a trailing point 186, corresponding in description to points 56, 58 described above. In this example, lead point 106 is collinear with outer surface 110 of needle body 98 while trailing point 108 is offset from outer surface 110 by a distance 112.

Figure 10:
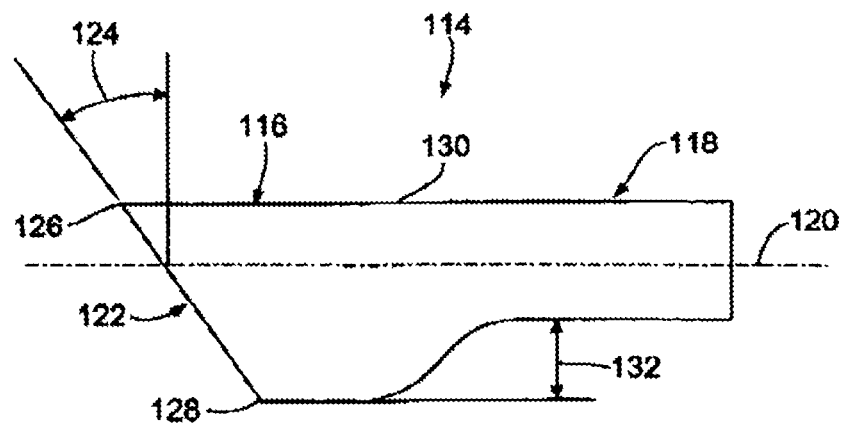
FIG. 10 is a partial lateral view of a variation of the tip shown in FIG. 6.

Referring now to FIG. 10 the numeral 114 identifies a phacoemulsification needle constructed substantially as described with respect to FIGS. 6, 7 and 8. Needle 114 has a tip 116 formed with a square cross-section and integral with needle body 118. Needle body 118 has a central axis 120.

Tip 116 has a square mouth 122 which, in this example, is formed at an angle 124 to axis 120. In this example, angle 124 is measured 30° in a direction opposite to that of angle 148 of mouth 74 as shown in FIG. 6. In this configuration, tip 114 has a lead lip portion 126 and a trailing lip portion 128, corresponding in description to lip portions 78, 80 described above. In this example, lead lip portion 126 includes a portion of outer surface 130 of needle body 118, i.e., is substantially coincident with an axially extending line at the outer surface 130 of needle body 118, while trailing lip portion 128 is offset from outer surface 110 by a distance 132.

Figure 11:
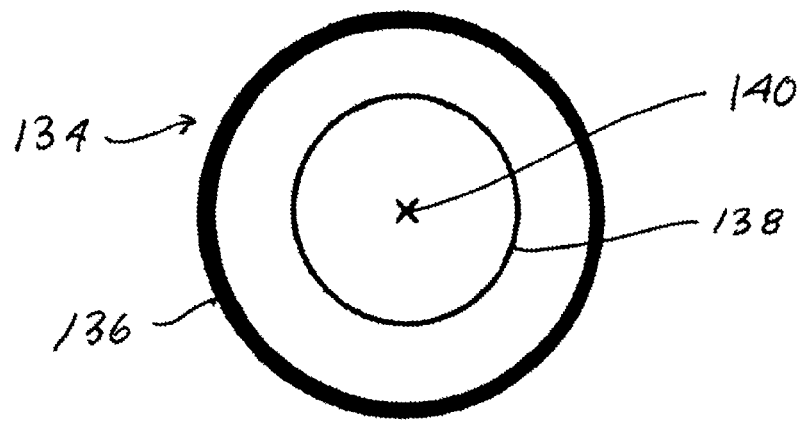
FIG. 11 is an illustration of the end of a prior art straight needle tip during torsional motion.
Figure 12:
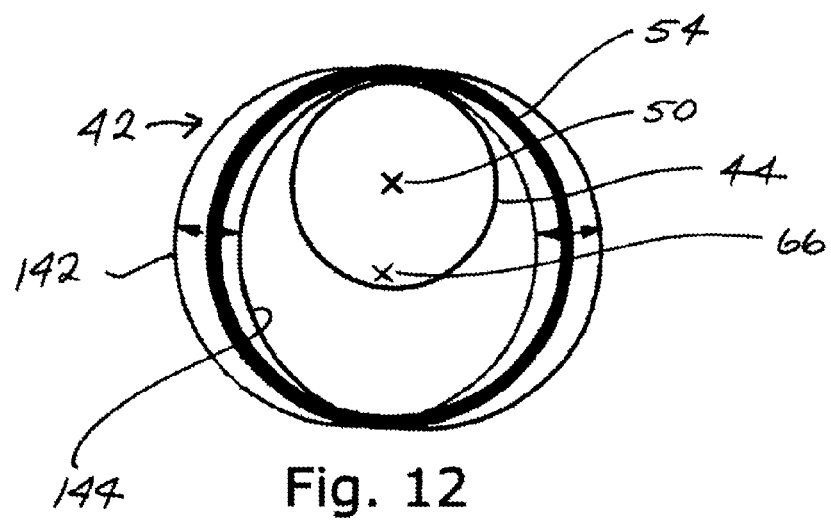
FIG. 12 is an illustration of the end of a needle tip constructed in accordance with the present invention and used with torsional motion.

The efficacy of having the tip axes in each of the foregoing examples be non-coincident with, or offset from, the needle body axes is demonstrated in FIGS. 11 and 12. Using a circular tip as an example, the numeral 134 in FIG. 11 identifies a prior art straight phacoemulsification tip having a circular cross-section defined by mouth 136 integral with and extending from needle body 138. Hollow needle body 138 has a central, longitudinally-extending axis 140. The geometry of tip 134 is such that axis 140 is also a central, longitudinally-extending axis for tip 134. When needle body 138 with tip 134 is attached to a phacoemulsification handpiece that produces torsional motion about axis 140 the pattern of vibration is generally as shown in FIG. 11, with tip 134 exhibiting little side-to-side or eccentric motion. In other words, lip 136 tends to rotate in a generally uniform motion about axis 140.

Referring now to FIG. 12, tip 42 of FIG. 5 is shown, with circular lip 54 and needle body 44 having needle body axis 50 and tip axis 66. When tip 42 is subjected to torsional rotation about axis 50 lip 48 moves eccentrically, or "wobbles" as it rotates, in part because tip 42's rotation is not centered on tip axis 66. This produces movement of lip 54 shown by paths 142 and 144, creating an enhanced cutting or emulsifying effect on the tissue contacted by tip 42. Thus, a straight phacoemulsification needle and tip can be used with a torsional phaco handpiece.

The "wobble" effect can be altered by changing the offset distance between the tip axis and the needle body axis, and by changing the geometry of the tip, by using different cross-sectional shapes such as triangular or polygonal.

While the needle bodies referred to in the foregoing examples have been referred to as circular in cross-section it should be understood that different cross-sectional shapes can also be used.

The foregoing examples have demonstrated round and square eccentric tips. Other tip cross-sectional shapes can also be used and the tips can be made with various orientations. For example, tip 70 can be rotated around tip axis 92 to create a different orientation. It is expected that the wobble effect will be manifested when the axis of the tip is offset from the axis of the needle body no matter what configuration is used.

Lips such as those shown at 50 and at 78 may also be polished to a smooth finish to add a protective feature. Phacoemulsification efficacy may also be enhanced by roughening a portion of the outer surface of the tips herein detailed.

I claim:

1. A phacoemulsification needle for use with a phacoemulsification handpiece capable of imparting a torsional, ultrasonic vibratory motion to said needle, said needle comprising:
   a hollow, elongate needle body having a proximal end, a distal end, and a central longitudinal axis extending between the proximal and distal ends;
   a mount at the proximal end configured to attach said needle body to a handpiece capable of imparting a torsional ultrasonic vibratory motion to said needle body, said needle body having a wall with an outer surface and an inner surface,
   said needle body inner surface defining a central passageway extending through said needle body from said proximal end to said distal end; and
   a needle tip at said distal end flaring radially outwardly from the outer surface of the needle body wall away from the central longitudinal axis at the distal end,
   said tip having an exterior surface and an interior surface, defining therebetween a tip wall comprising a first axially extending length,
   said tip wall terminating in a lip,
   said tip having a mouth defined by said lip,
   at least one portion of said tip having a cross-sectional shape normal to said central longitudinal axis of the needle body that is larger than a cross-sectional shape of at least a portion of the needle body normal to said central longitudinal axis of the needle body,
   said first axially extending tip wall length having a tip central longitudinal axis substantially parallel to said central longitudinal axis of the needle body,
   said central longitudinal axis of the needle body and said tip central longitudinal axis being radially offset one from the other, whereby an eccentric motion is imparted to said tip when a torsional, ultrasonic motion is imparted to said needle body through the handpiece attached at the proximal end of the needle body.

2. The needle as recited in claim 1 wherein said lip resides in a plane at an angle to a plane normal to said central longitudinal axis of the needle body.

3. The needle as recited in claim 2 wherein said angle is 30°.

4. The needle as recited in claim 1 wherein one of the tip exterior surface and the tip interior surface has a circular shape in cross-section normal to said tip central longitudinal axis of the tip wall length.

5. The needle as recited in claim 1 wherein one of the tip exterior surface and the tip interior surface has a square shape in cross-section normal to said tip central longitudinal axis of the tip wall length.

6. The needle as recited in claim 1 wherein said lip resides in a plane at an angle to a plane normal to said central longitudinal axis of the needle body, said lip having a lead portion and a trailing portion, said lead portion of said lip extending distally past said trailing portion.

7. The needle as recited in claim 6 wherein said angle is 30°.

8. The needle as recited in claim 6 wherein at least a part of said lead lip portion is substantially coincident with an axially extending line at said needle body outer surface.

9. The needle as recited in claim 6 wherein at least a part of said trailing lip portion is substantially coincident with an axially extending line at said needle body outer surface.

10. The needle as recited in claim 1 wherein said tip mouth has a cross-section shape normal to said tip central longitudinal axis of the tip wall length that is larger than a cross-sectional shape of said needle body normal to said central longitudinal axis of the needle body.

11. The needle as recited in claim 1 in combination with the handpiece to which the proximal end of the needle is mounted, the handpiece configured to impart a torsional, ultrasonic vibratory motion to said needle.

12. The needle as recited in claim 1 wherein the tip wall has a substantially uniform thickness around the lip.

13. A phacoemulsification needle for use with a phacoemulsification handpiece capable of imparting a torsional, ultrasonic vibratory motion to said needle, said needle comprising:
  a hollow, elongate needle body having a proximal end, a distal end, and a central longitudinal axis extending between the proximal and distal ends;
  a mount at the proximal end configured to attach said needle body to a handpiece capable of imparting a torsional ultrasonic vibratory motion to said needle body,
  said needle body having a wall with an outer surface and an inner surface,
  said needle body inner surface defining a central passageway extending through said needle body from said proximal end to said distal end; and
  a needle tip at said distal end flaring radially outwardly from the outer surface of the needle body wall away from the central longitudinal axis at the distal end,
    said tip having an exterior surface and an interior surface, defining therebetween a tip wall comprising a first axially extending length along which the tip has a cross-sectional shape normal to said central longitudinal axis of the needle body,
    said tip wall terminating in a lip,
    said tip having a mouth defined by said lip,
  at least one portion of said tip having a cross-sectional shape normal to said central longitudinal axis of the needle body that is larger than a cross-sectional shape of at least a portion of the needle body normal to said central longitudinal axis of the needle body,
  said first axially extending tip wall length having a tip central longitudinal axis substantially parallel to said central longitudinal axis of the needle body,
  said central longitudinal axis of the needle body and said tip central longitudinal axis being radially offset one from the other, whereby an eccentric motion is imparted to said tip when a torsional, ultrasonic motion is imparted to said needle body through the handpiece attached at the proximal end of the needle body.

* * * * *